US011217346B2

(12) United States Patent
Madonna et al.

(10) Patent No.: US 11,217,346 B2
(45) Date of Patent: Jan. 4, 2022

(54) SYSTEMS AND METHODS OF PROCESSING AND RECONCILING HEALTHCARE RELATED CLAIMS

(71) Applicant: Accumulation Technologies, LLC, Livonia, MI (US)

(72) Inventors: Andrew Madonna, Saline, MI (US); Benjamin Way, Canton, MI (US); Joshua Pearce, Northville, MI (US); Victor Tugulan, Redford, MI (US); John Eggertsen, Pittsfield Township, MI (US)

(73) Assignee: Accumulation Technologies, LLC, Livonia, MI (US)

( * ) Notice: Subject to any disclaimer, the term of this patent is extended or adjusted under 35 U.S.C. 154(b) by 339 days.

(21) Appl. No.: 16/163,219

(22) Filed: Oct. 17, 2018

(65) Prior Publication Data

US 2019/0115100 A1    Apr. 18, 2019

Related U.S. Application Data

(60) Provisional application No. 62/573,496, filed on Oct. 17, 2017.

(51) Int. Cl.
*G16H 10/60* (2018.01)
*G16H 40/20* (2018.01)
(Continued)

(52) U.S. Cl.
CPC .............. *G16H 40/20* (2018.01); *G06Q 30/04* (2013.01); *G16H 10/60* (2018.01); *G06Q 10/10* (2013.01); *G06Q 40/08* (2013.01)

(58) Field of Classification Search
CPC .......................... G16H 10/60; G06Q 50/22–24
See application file for complete search history.

(56) References Cited

U.S. PATENT DOCUMENTS

| 5,644,778 A | * | 7/1997 | Burks | G06Q 10/10 |
| | | | | 705/2 |
| 2002/0120473 A1 | * | 8/2002 | Wiggins | G06Q 20/102 |
| | | | | 705/4 |

(Continued)

FOREIGN PATENT DOCUMENTS

| WO | WO 2003/038564 | * | 5/2003 | ............. G06F 19/00 |

OTHER PUBLICATIONS

Medicare Claims Processing Manual; Jul. 2, 2015 (Year: 2015).*

*Primary Examiner* — John A Pauls

(74) *Attorney, Agent, or Firm* — Dinsmore & Shohl LLP

(57) ABSTRACT

Systems and methods for a computer machine system including one first computer memory having a first database and a second database. The first database is configured to store eligibility data for individuals associated a group healthcare plan, a set of user identifiers, one or more demographic information from the specific user, and one or more eligibility data. The second database is configured to store a plurality of rules for a claim submission associated with each group healthcare plan, originating payors associated with the claim submission, each originating payors having at least one data submission requirement associated with the claim submission, and a rule for a processed claim submission associated with each of the plurality of originating payors. The originating payors transmit the eligibility data for the individuals associated with the group healthcare plan such that the data submission requirement for each of the originating payors is mapped to the database.

17 Claims, 8 Drawing Sheets

(51) Int. Cl.
*G06Q 30/04* (2012.01)
*G06Q 10/10* (2012.01)
*G06Q 40/08* (2012.01)

(56) References Cited

U.S. PATENT DOCUMENTS

| | | | | |
|---|---|---|---|---|
| 2004/0073456 A1* | 4/2004 | Gottlieb | G06Q 10/10 | 705/2 |
| 2005/0065819 A1* | 3/2005 | Schultz | G06Q 10/10 | 705/2 |
| 2005/0102170 A1* | 5/2005 | Lefever | G06Q 30/02 | 705/4 |
| 2008/0027759 A1* | 1/2008 | Flam | G06Q 40/08 | 705/4 |
| 2011/0029321 A1* | 2/2011 | Rourke | G06F 16/986 | 705/2 |
| 2013/0132106 A1* | 5/2013 | Perry | G06Q 10/10 | 705/2 |
| 2013/0262154 A1* | 10/2013 | Whittier | G06Q 40/08 | 705/4 |
| 2016/0321124 A1* | 11/2016 | Baker | G06F 11/0745 | |
| 2017/0286495 A1* | 10/2017 | Ott | G06F 16/24578 | |

* cited by examiner

SYSTEMS AND METHODS OF PROCESSING AND RECONCILING HEALTHCARE RELATED CLAIMS

CROSS-REFERENCE TO RELATED APPLICATIONS

This application claims the benefit of U.S. Provisional Application No. 62/573,496, filed Oct. 17, 2017, the contents of which are included herein by reference.

TECHNICAL FIELD

The present disclosure generally relates to data integration and, more particularly, to systems and methods for data integration across multiple platforms and vendors for healthcare related claims.

BACKGROUND

The vast majority of healthcare expenses of individuals are partially or wholly paid for by entities that provide healthcare coverage ("Healthcare Risk Bearers"). These Healthcare Risk Bearers include employers and employee organizations (via sponsoring group health plans), health insurance companies (selling both individual and group policies), governments (e.g., Medicare and Medicaid), associations and many other entities. There are several types of health benefits provided by Healthcare Risk Bearers, such as hospital and doctor coverage, prescription drug coverage and mental health and substance abuse coverage. The Healthcare Risk Bearers establish demographic and benefit design requirements ("Eligibility Data") that the individuals must satisfy to qualify for the healthcare benefits the Healthcare Risk Bearers sponsors.

In order to pay healthcare providers' bills, Healthcare Risk Bearers usually hire claim processors ("Claim Processing Vendors"). Often Healthcare Risk Bearers hire different Claim Processing Vendors for different coverages. For example, a third party administrator may process hospital and doctor claims while a Pharmacy Benefit Manager would process drug claims. Sometimes several Claim Processing Vendors are hired for the same coverages and same individuals, especially over time.

The Claim Processing Vendors collect the Eligibility Data from the Healthcare Risk Bearers in preparation for receiving claims for payment from healthcare providers. When those claims are received, they are typically submitted and processed electronically. Once a claim has been adjudicated and processed by the applicable Claim Processing Vendor, information about the claim often should be communicated to several other Claim Processing Vendors who are working for the same Healthcare Risk Bearer ("Recipient Claim Processing Vendors"). In order for all Claim Processing Vendors to manage their portion of the Healthcare Risk Bearer's benefit, the Claim Processing Vendors need information about claims processed by other Claim Processing Vendors managing other aspects of the Healthcare Risk Bearer's benefit.

When multiple Claim Processing Vendors are involved in data integration, there are varying parameters for the data. Because of the varying membership and plan information used by each Claim Processing Vendor, processing failures can result. Each Recipient Claim Processing Vendor anticipates receiving claims only if the claim data matches their internal expectations. If those expectations are not met in full, the Recipient Claim Processing Vendor will fail to post the claim. With this failure, the originating Claim Processing Vendor and the Recipient Claim Processing Vendor will not be synchronized and will deliver an inconsistent experience to the individual covered by the Healthcare Risk Bearer based upon different data. To the originating Claim Processing Vendor, a claim data set would be considered legitimate and would be tagged within the originating Claim Processing Vendor's system as a legitimate claim but would not be so treated by the Recipient Claim Processing Vendor. The originating Claim Processing Vendor has no control over the Recipient Claim Processing Vendor system in order to override failures caused by data mismatches or inconsistencies. Instead, both Vendors must use resources to manually reconcile claim-posting errors between their systems. This manual process can incur a great expense and result in the inconsistent member experience existing for long periods of time.

Moreover, when a Claim Processing Vendor successfully processes a claim from a healthcare provider and wants to provide some of that information to a Recipient Claim Processing Vendor, it needs to do so in a format that meets the Recipient Claim Processing Vendor's requirements. For each claim, individual eligibility, group information and service eligibility must be provided in the proper format to be utilized by the Recipient Claim Processing Vendor. Charge reversals, partial adjustments, deductibles, copays and the like complicate the process. If all Claim Processing Vendors working for a Healthcare Risk Bearer (with respect to the same individuals) do not get the same eligibility data and claim payment information, errors can occur regarding, for example, eligibility and payment amounts. Many Claim Processing Vendors have not established communication links with other Claim Processing Vendors. Software and hardware incompatibility are the usual impediment. Confidentiality is also a widespread concern.

Accordingly, a need exist for systems and methods that can automatically reconcile claim posting errors between their systems and that can establish communication links between Claim Processing Vendors such that data integration may occur by transforming the data into a format that the Claim Processing Vendor and/or Recipient Claim Processing Vendor requires.

SUMMARY

In one embodiment, a computer machine system including one or more computer machines further includes at least one first computer memory having a first database and a second database. The first database is configured to store a plurality of eligibility data for a plurality of individuals associated a group healthcare plan, a set of user identifiers, wherein each user identifier is associated with a specific user, one or more demographic information from the specific user, and one or more eligibility data from said plurality of eligibility data. The second database is configured to store a plurality of rules for a claim submission associated with each group healthcare plan, a plurality of originating payors associated with the claim submission, each of the plurality of originating payors having at least one data submission requirements associated with the claim submission, and a plurality of rules for a processed claim submission associated with each of the plurality of originating payors. The plurality of originating payors transmit the plurality of eligibility data for the plurality of individuals associated with the group healthcare plan such that the at least one data submission requirement for each one of the plurality of originating payors is mapped to the database.

In another embodiment, a computer machine implemented automated claim processing method includes the steps of receiving, from at least one of a plurality of recipient payors, a members demographic information from a plurality of individuals associated a group healthcare plan, storing the members demographic information onto a first database, extracting from the stored demographic information, a plurality of required information for a claim submission to each of the plurality of recipient payors on a second database, mapping a received claim in the first database using the required information for the claim submission for each one of the plurality of recipient payors, and communicating to each one of the plurality of recipient payors the mapped information.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
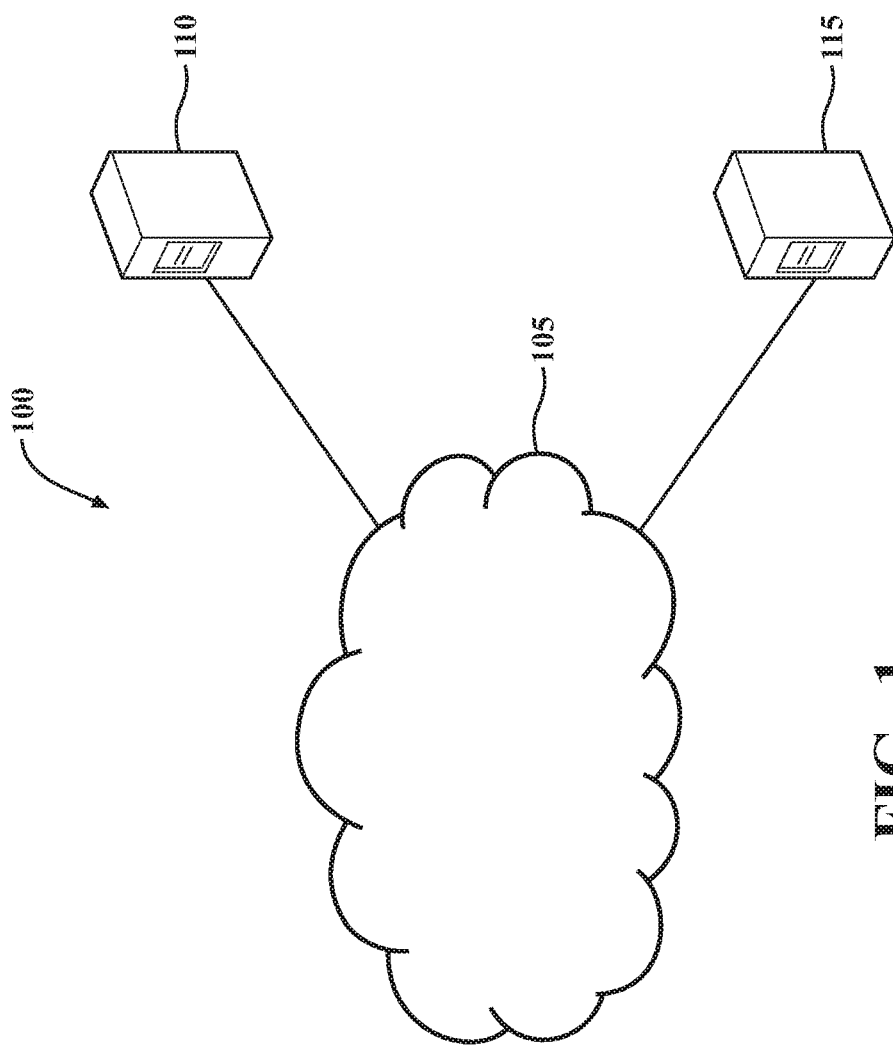
FIG. 1 schematically depicts a plurality of illustrative networked devices that may be used to provide a system for automated handling of claims among multiple Claim Processing and Recipient Vendors according to one or more embodiments shown or described herein.

Embodiments of the present disclosure are directed to systems and methods for an automated claim information exchange center ("Exchange Center") configured to facilitate data received into a database and preparing the data for data integration. The exchange system is configured to receive and provide data from multitudes of formats from different vendors and can manipulate the data into a standard format. The exchange system is configured to identify when vendors are out of sync with the system in real time.

As used herein, the terms "data," "content," "information" and similar terms may be used interchangeably to refer to data capable of being transmitted, received, displayed and/or stored in accordance with various example embodiments. Thus, use of any such terms should not be taken to limit the spirit and scope of the disclosure. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, and/or the like.

The term "computer-readable medium" as used herein refers to any medium configured to participate in providing information to a processor, including instructions for execution. Such a medium may take many forms, including, but not limited to a non-transitory computer-readable storage medium (for example, non-volatile media, volatile media), and transmission media. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Examples of computer-readable media include a floppy disk, a flexible disk, hard disk, magnetic tape, any other magnetic medium, a compact disc read only memory (CD-ROM), compact disc compact disc-rewritable (CD-RW), digital versatile disc (DVD), Blu-Ray, any other optical medium, punch cards, paper tape, optical mark sheets, any other physical medium with patterns of holes or other optically recognizable indicia, a random access memory (RAM), a programmable read only memory (PROM), an erasable programmable read only memory (EPROM), a FLASH-EPROM, any other memory chip or cartridge, a carrier wave, or any other medium from which a computer can read. The term computer-readable storage medium is used herein to refer to any computer-readable medium except transmission media. However, it will be appreciated that where embodiments are described to use a computer-readable storage medium, other types of computer-readable mediums may be substituted for or used in addition to the computer-readable storage medium in alternative embodiments.

As used herein, the term "Claim Processing Vendor" means any healthcare related claim processors or originating payors that may or may not be hired by or affiliated with the plan sponsor or healthcare risk bearer. Further, healthcare risk bearers generally hire different claim processing vendors for different coverages.

The term "Recipient Claim Processing Vendor" or recipient payors as used herein means that any healthcare related claim processors or originating payors that process the healthcare related claims and share this information about the claim or member to other claim processing vendors who are working for the same healthcare risk bearer.

Now referring to FIG. 1, an exchange center system 100 for facilitating data received into a database and preparing the data for data integration according to an example embodiment is depicted. The exchange system, or computer system, generally designated 100, includes, but is not limited to, a computer network 105 that is generally configured to electronically connect one or more server computing devices 110, 115.

The computer network 105 may include any network now known or later developed, including, but not limited to, a wide area network (WAN), such as the Internet, a local area network (LAN), a mobile communications network, a public service telephone network (PSTN), a personal area network (PAN), a metropolitan area network (MAN), a virtual private network (VPN), or any combination thereof.

The one or more server computing devices 110, 115 may receive electronic data and/or the like from one or more sources (e.g., one or more user computing devices), create a data format, a plurality of coding standards, a plurality of connectivity information, and establish a transmission record, as discussed in greater detail herein. In some embodiments, the one or more server computing devices 110, 115 may function as management devices. Accordingly, in some embodiments, the one or more server computing devices 110, 115 may control a right or an ability to enter an additional data into a database, as described in greater detail herein.

It should be understood that while the one or more server computing devices 110, 115 are depicted as servers, these are non-limiting examples. More specifically, in some embodiments, any type of computing device (e.g., mobile device, tablet computing device, personal computer, server, etc.) may be used for these components. Additionally, while each of the server computing devices 110, 115 are illustrated in FIG. 1 as a single piece of hardware, this is also merely an example. More specifically, each of the one or more server computing devices 110, 115 may represent a plurality of computers, servers, databases, components, and/or the like.

It will be appreciated that the system 100 as well as the illustrations in other figures are each provided as an example of one embodiment and should not be construed to narrow the scope or spirit of the disclosure in any way. In this regard, the scope of the disclosure encompasses many potential embodiments in addition to those illustrated and described herein. As such, while FIG. 1 illustrates one example of a configuration of a system for facilitating data received into a database and preparing the data for data integration, numerous other configurations may also be used to implement embodiments of the present invention.

Figure 2A:
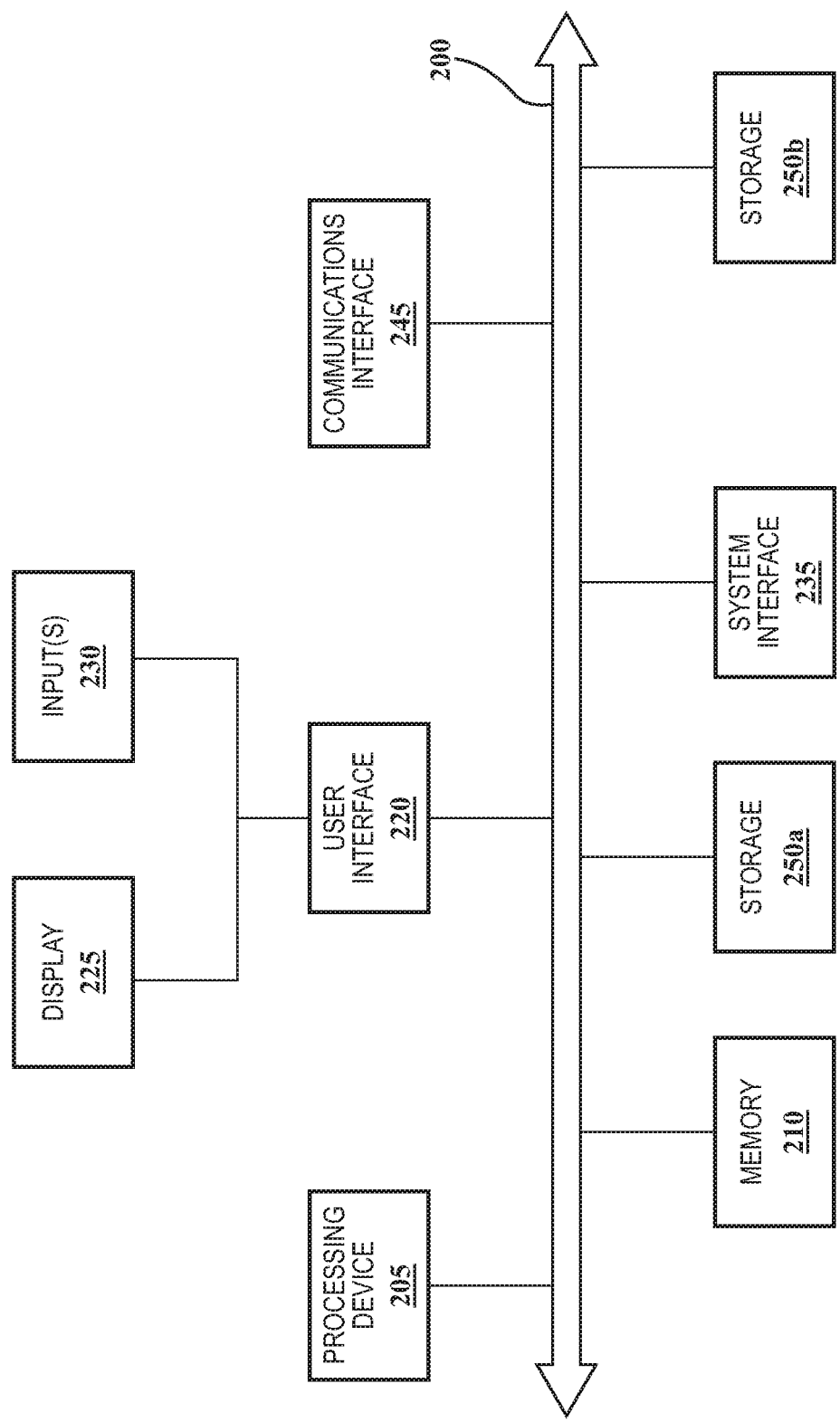
FIG. 2A schematically depicts a block diagram of illustrative computing device components according to one or more embodiments shown or described herein.

Illustrative hardware components of each one of the one or more server computing devices 110, 115 are depicted in FIG. 2A. That is, the hardware components depicted in FIG. 2A may be present in any one of the one or more server computing devices 110, 115 or other devices not depicted in FIG. 1. A bus 200 may interconnect the various components. A processing device 205, such as a computer-processing unit (CPU), may be the central processing unit of the computing device, performing calculations and logic operations required to execute a program. The processing device 205, alone or in conjunction with one or more of the other elements disclosed in FIG. 2A, is an illustrative processing device, computing device, processor, or combination thereof, as such terms are used within this disclosure. Memory 210, such as read only memory (ROM) and random access memory (RAM), may constitute illustrative memory devices (i.e., non-transitory processor-readable storage media). Such memory 210 may include one or more programming instructions thereon that, when executed by the processing device 205, cause the processing device 205 to complete various processes, such as the processes described herein. Optionally, the program instructions may be stored on a tangible computer-readable medium such as a compact disc, a digital disk, flash memory, a memory card, a USB drive, an optical disc storage medium, such as a Blu-ray™ disc, and/or other non-transitory processor-readable storage media now known or later developed.

Figure 2B:
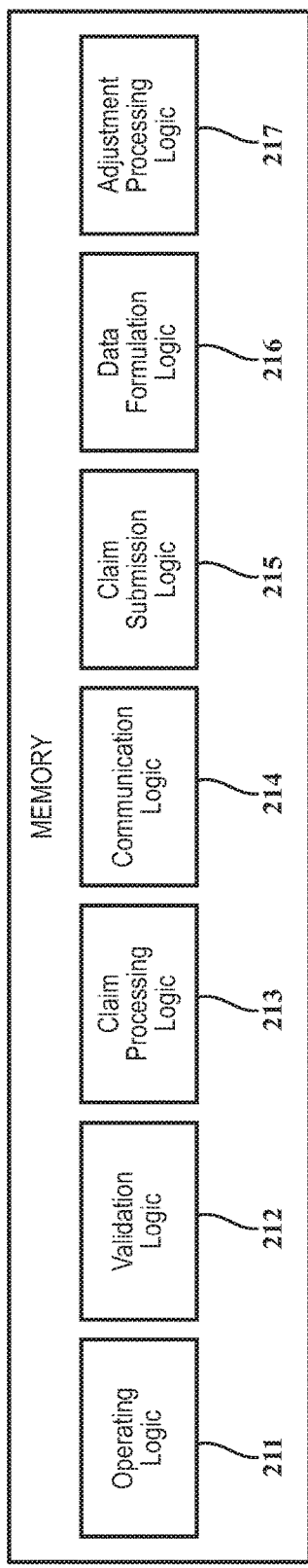
FIG. 2B schematically depicts a block diagram of illustrative logic modules that may be contained within a memory of a computing device according to one or more embodiments shown and described herein.

In some embodiments, the program instructions contained on the memory 210 may be embodied as a plurality of software modules, where each module provides programming instructions for completing one or more tasks. For example, as shown in FIG. 2B, the memory 210 may contain one or more of operating logic 211, validation logic 212, claim processing logic 213, communications logic 214, claim submission logic 215, data formulation logic 216, and adjustment processing logic 217. The operating logic 211 may include an operating system and/or other software for managing components of a computing device or electronic device. The validation logic 212 may include software or the like for validating an incoming healthcare related claim, determining whether a member record exists, deciding whether of a plurality of eligibility data matches an existing member data, and/or the like. The claim processing logic 213 may include software or the like for storing a plurality of rules for a claim submission associated with each Claim Processing Vendors, transmits the plurality of eligibility data for the plurality of individuals associated with the Healthcare Risk Bearers plan, mapping at least one data submission requirement for each one of the plurality of Claim Processing Vendors to the central database, and/or the like. The communications logic 214 may include software or the like that allows communication between the server computing devices 110, 115, the network 105, and various other components for the purposes of transmitting or receiving data and/or data related to a healthcare claim, a portion of a healthcare claim, transmitting or receiving communications relating to adjustment data for healthcare related claims, and/or the like. The claim submission logic 215 may include software or the like for extracting from a stored demographic information a plurality of required information for a claim submission to each of the plurality of Recipient Claim Vendors, analyzing the healthcare claim data to determine whether or not the healthcare claim will be accepted by the plurality of Recipient Claim Vendors, transmitting to the at least one of the plurality of Recipient Claim Vendors if the healthcare related claim will be accepted, staging the healthcare related claim if the claim will not be accepted by the Recipient Claim Vendors, and/or the like.

The data formulation logic 216 may include software or the like for manipulating data related to the healthcare claim so to place the data into a condition to be accepted by the Claim Processing Vendor and/or the Recipient Claim Processing Vendor. The adjustment processing logic 217 may include software or the like for partial adjustments, full reversals, and/or the like, some based on whether there is a claim ID reference, claim reference number, or an identifier, and in some embodiments, creating the chain of claims, as will be discussed in greater detail herein.

It should be understood that the various logic modules described herein with respect to FIG. 2B are merely illustrative, and that other logic modules, including logic modules that combine the functionality of two or more of the modules described hereinabove, may be used without departing from the scope of the present application.

Referring again to FIG. 2A, a central storage device 250*a*, which may generally be a storage medium that is separate from the memory 210, may contain a data repository for storing data that is used for storing electronic data and/or the like relating to a plurality of eligibility data for a plurality of individuals or members associated with the Healthcare Risk Bearers, or a group healthcare plan, a set of user identifiers that may be associated with a specific user or member, one or more demographic information from the specific user or member, one or more eligibility data from said plurality of eligibility data, and/or the like, as will be discussed in greater detail herein. The central storage device 250a may be any physical storage medium, including, but not limited to, a hard disk drive (HDD), memory, removable storage, and/or the like.

The repository storage device 250b, which may generally be a storage medium that is separate from the memory 210 and the central storage device 250a, may contain a data repository for storing data that is used for storing electronic data relating to a plurality of rules for a claim submission associated with each group of the group health care plans, a plurality of Claim Processing Vendors, or originating payors, associated with the claim submission, at least one data submission requirements associated with each of the plurality of Claim Processing Vendors, a plurality of rules for a processed claim submission associated with each of the plurality of Claim Processing Vendors, at least one data submission requirement associated with the processed claim submission associated with each one of a plurality of Recipient Claim Processing Vendors, or recipient payors, and/or the like, as will be discussed in greater detail herein. The repository storage device 250b may be any physical storage medium, including, but not limited to, a hard disk drive (HDD), memory, removable storage, and/or the like.

Figure 2C:
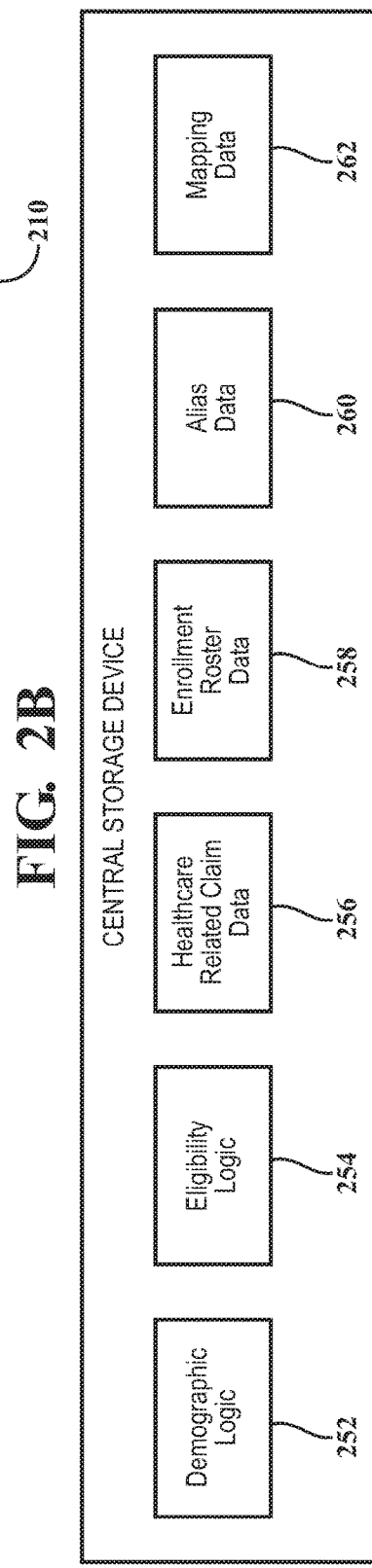
FIG. 2C schematically depicts a block diagram of illustrative types of data that may be contained within a central data storage component of a computing device according to one or more embodiments shown and described herein.

Illustrative data that may be contained within the central storage device 250a is depicted in FIG. 2C. As shown in FIG. 2C, the central storage device 250a may include, for example, demographic data 252, eligibility data 254, healthcare related claim data 256, enrollment roster data 258, aliases data 260, and mapping data 262. Demographic data 252 may include, for example, a set of user identifiers associated with a specific user or member, one or more demographic information about the specific user or member, and/or the like. Eligibility data 254 may include, for example, data relating to the specific user or member and the Healthcare Bearer Risk, or group healthcare plan, such as data relating to a plurality of co-pays and a plurality of deductibles, and/or the like. Healthcare related claim data 256 may include, for example, data related to the healthcare claim. This data may be stored in a new claim table and to a common claims table as discussed in greater detail below. Enrollment roster data 258 may include, for example, data related the enrollment of a plurality of users or members in the group healthcare plan. Aliases data 260 may include, for example, data related to the plurality of users or members who have some variation from the enrollment roster data 258 and/or demographic data 252, as discussed in greater detail herein. Mapping data 262 may include, for example, data related to the healthcare related claim that is mapped to the repository storage device 250b in a format that each one of the plurality of Recipient Claim Vendors may accept, as discussed in greater detail herein.

Figure 2D:
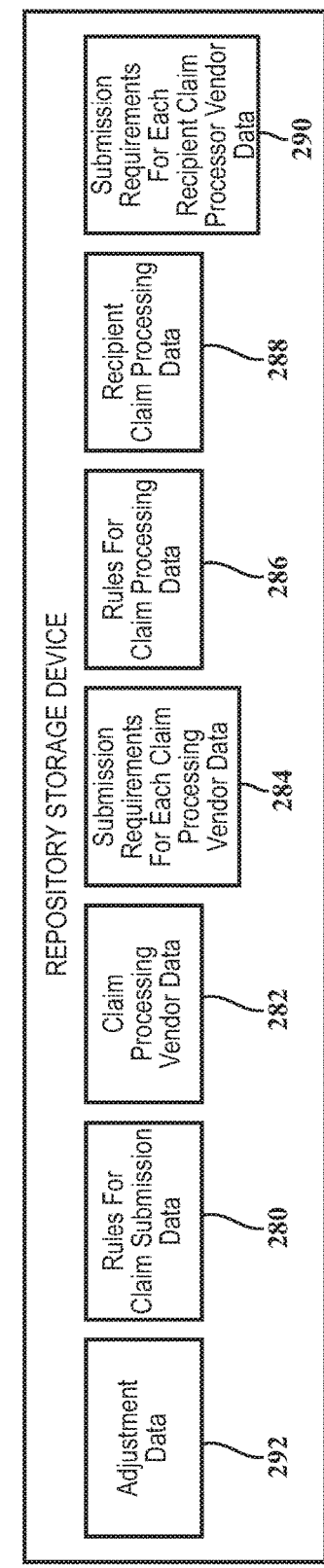
FIG. 2D schematically depicts a block diagram of illustrative types of data that may be contained within a repository data storage component of a computing device according to one or more embodiments shown and described herein.

Illustrative data that may be contained within the repository storage device 250b is depicted in FIG. 2D. As shown in FIG. 2D, the repository storage device 250b may include, for example, rules for a claim submission data 280, Claim Processing Vendors data 282, data submission requirements associated with each Claim Processing Vendors data 284, rules for a processed claim submission data 286, Recipient Claim Processing Vendors data 288, data submission requirements associated with each Recipient Claim Processing Vendors data 290, and adjustment data 292. Rules for claim submission data 280 may include, for example, data related to healthcare related claims posting. Claim Processing Vendors data 282 may include, for example, data related to identify each one of a plurality of Claim Processing Vendors. Data submission requirements associated with each Claim Processing Vendor data 284 may include, for example, data related to a specific format that the healthcare related claim, including member information, demographic information, eligibility information, and/or the like, is required for submission. Rules for a processed claim submission data 286 may include, for example, data related to processing the healthcare related claim based on predetermined criteria established by the Claim Processing Vendor. Recipient Claim Processing Vendors data 288 may include, for example, data related to identify each one of a plurality of Recipient Claim Processing Vendors. Data submission requirements associated with each Recipient Claim Processing Vendors data 290 may include, for example, data related to a data format, a plurality of coding standards, a plurality of connectivity information, and a manner in which the claim submission is forwarded to the plurality of Recipient Claim Processing Vendors. Adjustment data 292 may include, for example, data relating to an adjustment to the healthcare related claim such as a partial adjustment, a reversal to the healthcare related claim, and/or the like as will be discussed in greater detail herein.

Referring again to FIG. 2A, an optional user interface 220 may permit information from the bus 200 to be displayed on a display 225 portion of the computing device in audio, visual, graphic, and/or alphanumeric format. Moreover, the user interface 220 may also include one or more inputs 230 that allow for transmission to and receipt of data from input devices such as a keyboard, a mouse, a joystick, a touch screen, a remote control, a pointing device, a video input device, an audio input device, a haptic feedback device, and/or the like. Such a user interface 220 may be used, for example, to allow a user to interact with the computing device, electronic device, or any component thereof.

A system interface 235 may generally provide the device with an ability to interface with one or more of the components of the exchange center system 100 (FIG. 1). Communication with such components may occur using various communication ports (not shown). An illustrative communication port may be attached to a communications network, such as the Internet, an intranet, a local network, a direct connection, and/or the like. As described in further detail herein, such communication may allow for a decentralized ledger for maintaining agreements among users in an open-science community.

A communications interface 245 may generally provide the server computing devices 110, 115 with an ability to interface with one or more external components, such as, for example, an external computing device, a remote server, and/or the like that is external to the exchange center system 100 (FIG. 1). Communication with external devices may occur using various communication ports (not shown). An illustrative communication port may be attached to a communications network, such as the Internet, an intranet, a local network, a direct connection, and/or the like.

It should be understood that in some embodiments, the system interface 235 and the communications interface 245 may be combined into a single device that allows for communications with other devices, regardless of whether such other devices are located within the exchange center system 100 (FIG. 1).

It should be understood that the components illustrated in FIGS. 2A-2D are merely illustrative and are not intended to limit the scope of this disclosure. More specifically, while the components in FIGS. 2A-2D are illustrated as residing within one or more of the server computing devices 110, 115 these are non-limiting examples. In some embodiments, one or more of the components may reside external to one or more of the server computing devices 110, 115 such as in user-facing computer devices such as desktop computers, laptops, tablets, and/or the like. Similarly, one or more of the components may be embodied in other computing devices not specifically described herein.

Figure 3:
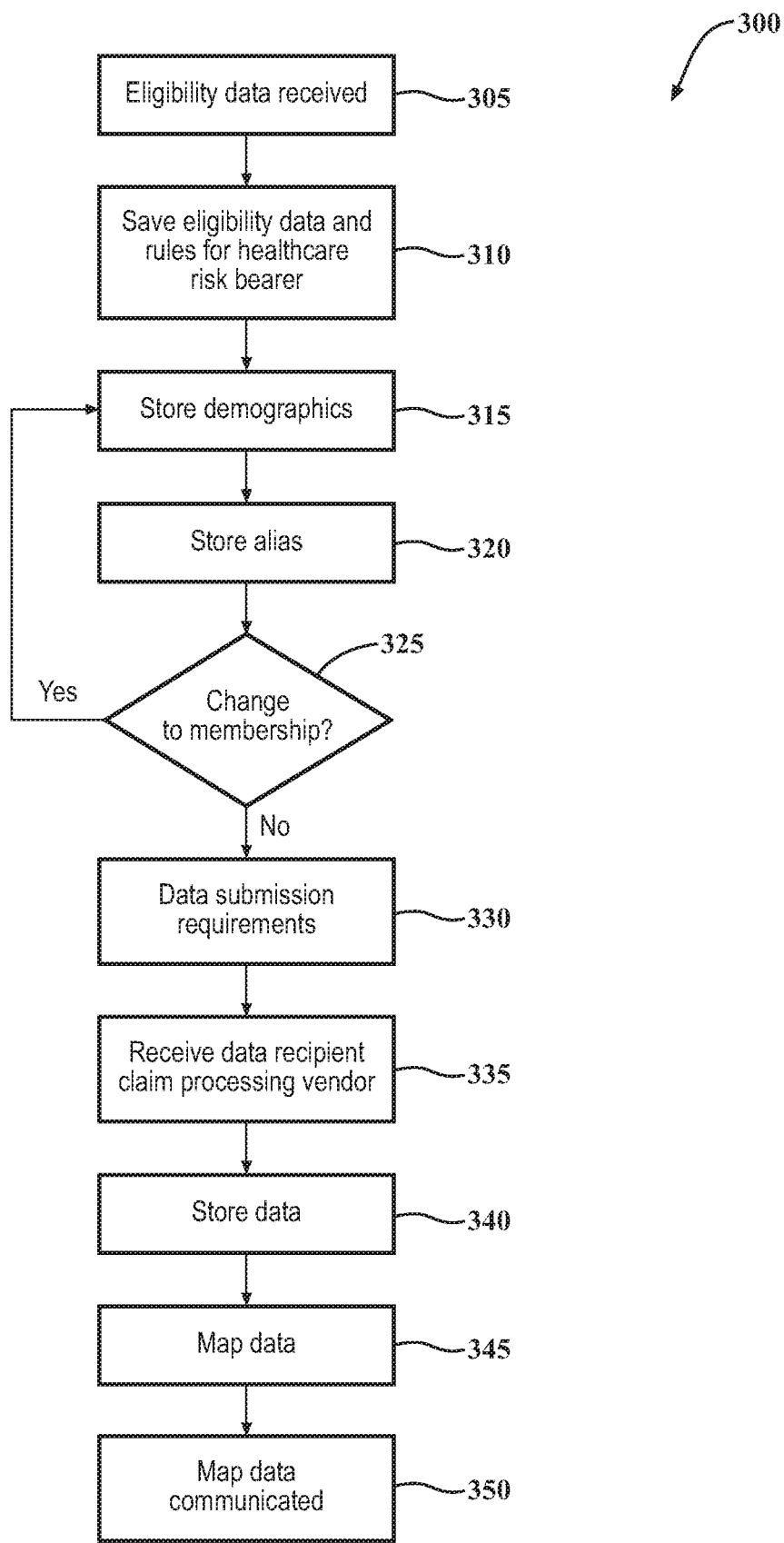
FIG. 3 depicts a flow diagram of an illustrative method of obtaining and populating the storage devices in the exchange center system of FIG. 1 according to one or more embodiments shown or described herein.

FIG. 3 depicts a flow diagram of an illustrative method of obtaining and populating the storage devices 250*a*, 250*b* in the exchange center system 100. The eligibility data is received by exchange center system 100 from the Claim Processing Vendor, at block 305, for each of the HealthCare Risk Bearer's benefits that that Claim Processing Vendor manages. The eligibility data and rules of each Healthcare Risk Bearer are stored in the central storage device 250*a* at block 310. The exchange center system 100 stores a plurality of demographic information relating to each individual or member for each specific HealthCare Risk Bearer at block 315.

The exchange center system 100 also stores a list of aliases, at block 320. The list of aliases contains all of the variants of the individual's or members demographics that appear for that individual or member in that Claim Processing Vendor's enrollment roster. The exchange center system 100 determines, at block 325, whether a change to the membership has occurred. If there is a change to the membership then the change in the demographics is stored at block 315. It should be appreciated that the exchange center system 100 maintains a list of membership changes over time to ensure that the healthcare related claims delivered to the storage devices 250*a*, 250*b* will appropriately match the individual's eligibility data between Claim Processing Vendors regardless of which set of demographic data is delivered by the source or originating Claim Processing Vendor. Further, it should be appreciated that individuals or members may have several alias records for each Claim Processing Vendor. Because coverage of individuals by HealthCare Risk Bearers for each Claim Processing Vendor is processed and stored in the storage devices 250*a*, 250*b*, the individual's or members data for that individual's claim received from an originating Claim Processing Vendor is compared automatically. As such, the system 100 is configured to map the information for the individual or member from one Claim Processing Vendor to other Claim Processing Vendors for that Healthcare Risk Bearer, which keeps accessing the list of all aliases used by that specific Vendor at block 320.

Therefore, this mapping or crosswalk created in the repository storage device 250*b* between each integrated Claim Processing Vendor is used for other processes. In some embodiments, the crosswalk may be required when subsequent adjustments are received from the originating Claim Processing Vendor. Without the appropriate reference information provided by the crosswalk, the recipient vendor will typically reject incoming adjustment records. Thus, the system 100 establishes a set of processing rules for each Claim Processing Vendor based on its method of processing claim adjustments, as discussed in greater detail herein The rules are then used to generate a reference map for each Claim Processing Vendor. When an adjustment is received from originating Claim Processing Vendor, the system accesses the reference map for the Recipient Claim Processing Vendor to determine the manner in which the claim will be submitted to Recipient Claim Processing Vendor so to ensure adjustments are built to the specifications in the Recipient Claim Processing Vendor's system. The system monitors the entire chain of adjustments involved in the claim so that future adjustments or reversals of these claims are assigned appropriate cross-reference codes, or claim reference numbers as discussed in greater detail herein. The claim reference numbers may be necessary because generally Claim Processing Vendor systems cannot accept adjustment or reversal claims without having a reference to the original claim. Therefore, if the system 100 receives an adjustment claim without receiving the original claim, the system 100 will hold or recycle review the claim until the proper original claim is received, as discussed in greater detail herein.

In addition to a roster of all alias records that exist for an individual or member in the data files of each Claim Processing Vendor, a flag denotes which alias is most current for each Claim Processing Vendor. Recipient Claim Processing Vendors may be much more likely to successfully process data if the most current demographic information from the recipient vendors system is provided within the record sent, as discussed in greater detail herein.

Each Claim Processing Vendor's data submission requirements are stored into the into the repository storage device 250*b* at block 330. As discussed above, the submission requires may include the data format that the healthcare related claim is required, coding standards, connectivity information, the manner in which claims are to be forwarded to Recipient Claim Processing Vendors, and/or the like. As such, the exchange center system 100 utilizes the storage devices 250*a*, 250*b* and logic algorithm or method 400 (FIG. 4) to determine to which Recipient Claim Processing Vendor each claim is to be forwarded based upon the rules for each Healthcare Risk Bearer.

The exchange center system 100 stores information received from each Recipient Claim Processing Vendor at block 335 including the member's demographic information, plan details, type of service provided and other relevant details like cost. This information is stored into the central storage device 250*a*, at block 340, from which the information necessary to forward claim details can be withdrawn. The exchange center system 100 maps each received healthcare related claim in the storage devices 250*a*, 250*b*, at block 345, using the claim submission requirements for each Recipient Claim Processing Vendor. It should be appreciated that without the mapping, the Recipient Claim Processing Vendor may not successfully post the healthcare related claim using the Recipient Claim Processing Vendors standard system. The information is communicated to a Recipient Claim Processing Vendor, at block 350, for tracking, cost integration, clinical or other purposes. Each Claim Processing Vendor and Recipient Claim Processing Vendor expects that the membership and plan eligibility information it provided to the exchange center system should match that Claim Processing Vendor's internal data.

Claims submitted by the originating Claim Processing Vendor are posted in the central repository database and claims meeting a Recipient Claim Processing Vendor's standards are released for transmission to the Recipient Claim Processing Vendor. Claims that post but fail to meet a Recipient Claim Processing Vendor's standards are held until sufficient data is provided to permit successful posting, as will be discussed in greater detail herein. It should be appreciated that the exchange center system 100 is configured to use the data stored as described herein to use as an automated process for integration of co-pays and deductibles that apply to the different coverages, establishing and managing claim reversals and adjustments based upon the specific requirements for each Recipient Claim Processing Vendor, and/or the like, as will be discussed with reference to the method 400 (FIG. 4).

Figure 4:
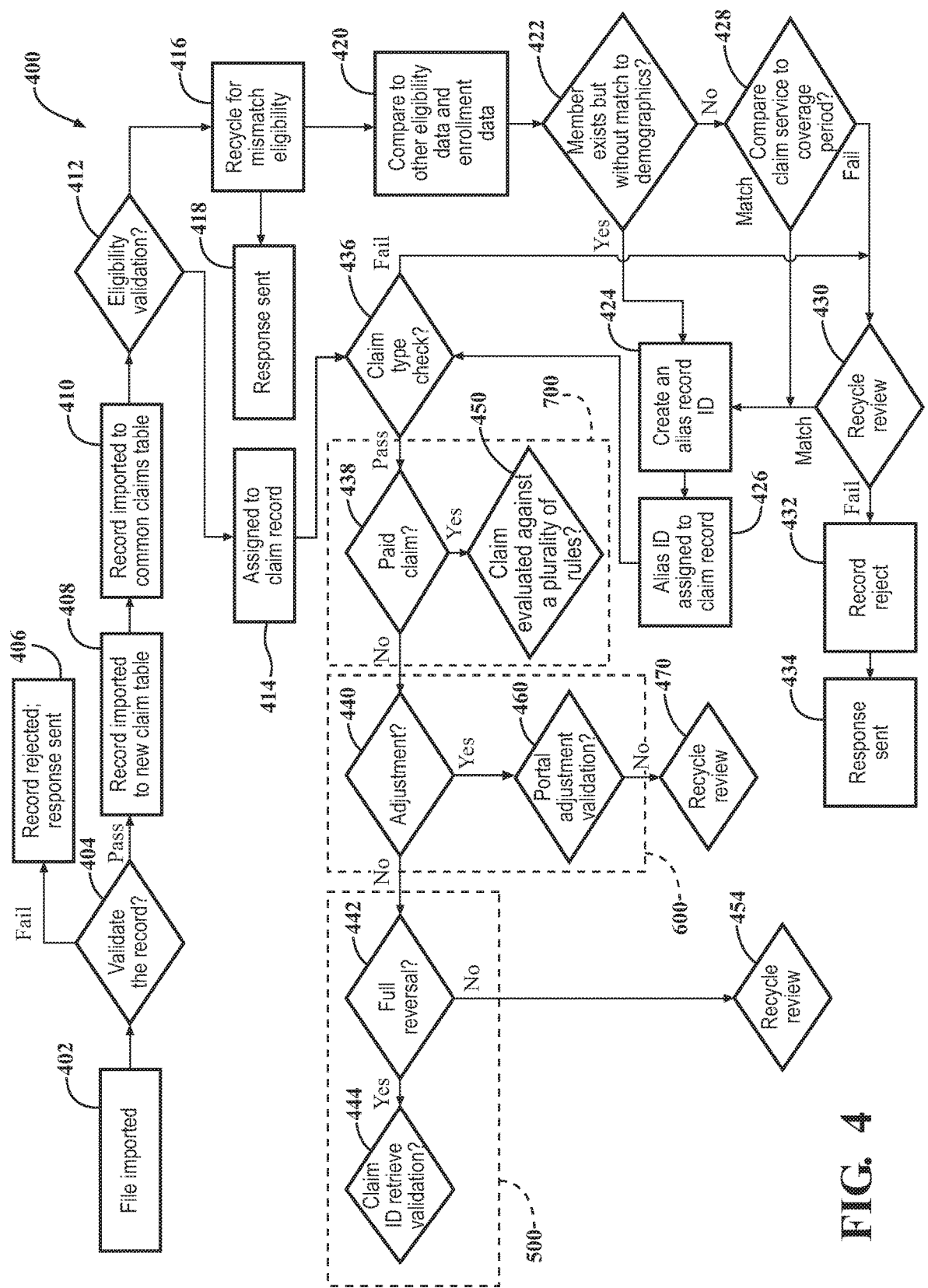
FIG. 4 depicts a flow diagram of an illustrative method of processing a healthcare related claim, or record, in the exchange center system according to one or more embodiments shown and described herein

FIG. 4 depicts a flow diagram of an illustrative method of processing a healthcare related claim, or record, in the exchange center system 100. The exchange center system 100 receives the healthcare related claim known as the file imported, at block 402 from the originating Claim Processing Vendors. The different vendors that send the healthcare related claims to the exchange center system 100 generally have different formats for the claims which increase the difficulty for these entities to properly communicate. That is, the originating Claim Processing Vendors generally transmit or send data including the healthcare related claim in the same format that the Claim Processing Vendors are currently using. As such, the exchange center system 100 is configured to validate the record, at block 404, so to determine whether the structure of the data matches an expected layout.

That is, the exchange center system 100 pulls in the layout that each Claim Processing Vendor is using, extracts the data and then stores into the coded layout schema into the storage devices 250a, 250b so that the data is taken from each Claim Processing Vendor may be adjusted and prepared to be sent to a another vendor, entity, and/or the like, as discussed in greater detail below. It should be appreciated that the data is validated not only for the expected layout, but also that the data elements make sense for their data type (i.e. a date field does not contain a date in the year 25,000 or a dollar amount does not contain letters), and/or the like. This is the first check that the exchange center system 100 performs of the data.

As such, if the structure of the data fails the validation at block 404, the record may be rejected and a response may be sent to the originating Claim Processing Vendor explaining the same at block 406. On the other hand, if the structure of the data passes the validation at block 404, the record may be imported to a raw claims table at block 408 and the record may be imported to a common claims table at block 410. It should be appreciated that the common claims table is transforming and/or normalizing data received by the system that is stored to the raw claims table at block 408. As such, it should be appreciated that because the data incoming to the system 100 is in a plurality of formats and contains a plurality of data elements, the system 100, using a Structured Query Language (SQL) database and/or the like, converts the data stored in the claim table of block 408 to a standard or common format. As such, each claim may be stored as its own row within the claims table.

The exchange center system 100 next performs an eligibility validation of the record at block 412. The eligibility validation is completed by using the incoming record and matching the data of the incoming record to a known individual. The comparison is accomplished by comparing the data from the record to the eligibility information previously submitted by the originating Claim Processing Vendor and stored in the central storage device 250a. If a match is found between the data of the incoming record to the known individual, then the known individual data is assigned to the record at block 414. If a match is not initially found, the exchange center system 100 recycles the record for a mismatched eligibility at block 416 while sending a response to the originating Claim Processing Vendor explaining the same at block 418.

Further, the record is compared to eligibility data, enrollment data from other originating Claim Processing Vendors, internal data stored in the exchange center system 100, and/or the like in order to establish whether the data of the current claim record may be a variation from any other known records to individuals at block 420. As such, if the member exists but some changes to the basic demographic information are detected at block 422, a new alias record will be created at block 424 and the alias ID will be assigned to the claim record at block 426. It should be appreciated that recorded aliases for a member may be stored to keep a reference to any previously viewed data for that member.

It should also be appreciated that the exchange center system 100 builds and maintains a comprehensive coverage history for each individual covered by a Healthcare Risk Bearer based on eligibility changes that occur over time. For each such individual, a separate history may be kept for each Claim Processing Vendor. The exchange center system 100 may also record any Claim Processing Vendor specific setup information that would be required to successfully post the claim record when the healthcare service date falls within a coverage period. This may include group, benefit or information about services dates. In some cases, Claim Processing Vendors may only accept healthcare related claims that fall within their approved coverage periods. The coverage history allows the system to determine whether a claim meets those eligibility requirements for each Claim Processing Vendor. As such, internal data stored may include individual information on each Claim Processing Vendor, coverage periods and the associated Eligibility Data.

As such, the eligibility validation of block 412 may fail based not only with individual and eligibility mismatches, but also with claim coverage mismatches. Therefore, if the mismatch is not based on demographics at block 422, the claim service date may be compared against the Claim Processing Vendor's coverage period information in the coverage history at block 428. If there is not a coverage period match, the claim may be held in the recycle review at block 430. If a claim coverage match can be confirmed, the new alias record may be created at block 424 and the alias ID may be assigned to the claim record at block 426.

It should be appreciated that exchange center system 100 recycles records at block 430 when the exchange center system 100 is unable to successfully process the claim for a variety of reasons (i.e. eligibility mismatch at block 412, claim coverage period mismatch at block 428, and/or the like). While recycling, the exchange center system 100 monitors for changes that could remedy or fix the error that caused the claim to be placed into the recycle review at block 430. It should be appreciated that this process may be automatic (i.e. without human intervention) and may be accomplished using supervised or unsupervised machine learning. By way of an example and not limiting, a claim record that is in the recycle review at block 430 for failing the eligibility validation at block 412, the exchange center system 100 would monitor for any eligibility update and would automatically reprocess that claim from block 412 the next time an eligibility update is received. That is, after receiving the eligibility update, the exchange center system 100 automatically determines if the update provides the information required to tie that claim to the exchange center system 100 by having a match at block 412 or block 422 so that an alias ID may be created at block 424. It should be appreciated that the alias ID may be a variation of a current member record, a new member record, and/or the like.

It should also be appreciated that throughout the method 400 described above, and in particular the recycle review loop at block 430, the exchange center system 100 retains the Healthcare Risk Bearer's Eligibility Data submitted by the different Claim Processing Vendors servicing that Healthcare Risk Bearer. As such, when the Eligibility Data is compared across Claim Processing Vendors, a list of discrepancies is compiled that may include individuals existing in the Eligibility Data roster at one Claim Processing Vendor but not in others or individuals existing on both rosters but with disparate dates of eligibility or benefit information. These discrepancies are reported directly to the Healthcare Risk Bearer so it can advise the proper action to resolve the discrepancy. As the Healthcare Risk Bearer acts as the arbiter of its eligibility, it will have to advise in each instance which Claim Processing Vendor needs to correct their data. When these issues are resolved, updated eligibility data will be delivered to the system 100 so that a match at block 412 or block 422 occurs and the held claim is released, as discussed in greater detail above.

It should be appreciated that the recycle review at block 430, as discussed above, continues to loop through a recycle period that can be adjustable. By way of an example and not limiting, the recycle period may be 30 days for one Vendor, 60 days for another Vendor, and/or the like such that predetermined time periods for how long the claim may be recycled. Once the predetermined time period is exhausted without the claim record leaving the recycle review loop, the claim or record is rejected at block 432 and a rejection response is provided back to the originating Claim Processing Vendor's at block 434. The response to the originating Claim Processing Vendor may include a reason for the rejection. By way of an example and not limiting, the response may include the reason of rejection being due to mismatched eligibility. As such, once the claim is rejected at block 432, the originating Claim Processing Vendor would again be responsible for the claim and for correcting the reasoning for why the claim failed.

On the other hand, once matched, regardless of whether by the alias ID at block 424 or if the record passed the eligibility validation at block 412, the claim type is checked for an adjustment at block 436. The three types of adjustment processing that occur are the full reversal model, the partial adjustment model and the manual adjustment model. As such, the claim is checked to determine whether the claim is the paid claim at block 438, the partial adjustment claim at block 440, the full reversal claim at block 442, or, if the claim type is not available. If the claim type is not available at block 436 then the claim is sent to the recycle review at block 430. The full reversal model is used to reverse a paid claim to balance out the cost share to zero. The exchange center system 100 uses reference information and other information in claims fields to identify those claims. As such, the claim record is validated for a claim ID reference at block 444.

Further details concerning the full reversal claim at block 442 will now be discussed with reference to illustrative method 500 in FIG. 5. If the claim reference is found within the system 100 (i.e. in the storage devices 250a, 250b), then the claim reference is added and the claim is evaluated against a plurality of rules at block 450. The plurality of rules may include a cross check of the reference ID to the saved claim reference ID, the claim record may be verified against a set of rules established by Claim Processing Vendors or the Recipient Claim Processing Vendors so that the claim reversal is applied to the proper claim or is in the correct format, and/or the like. If the claim passes the plurality of rules at block 450, the claims reference is added and the claim record is accepted at block 446, a response is sent to the Claim processing Vendors and/or the Recipient Claim Vendors indicating and transferring of the money reversal at block 448, the claim is staged for export at block 482, and the record is extracted for delivery to the vendor at block 484. By way of example and not limiting, if the original claim was for $10.00, a full reversal was requested for the −$10.00 at block 442, the exchange center system 100 would accept the claim reference at block 446, deliver the message and the $10.00 claim at block 448 and the $10.00 reversal would be directed to the recipient vendor at block 484.

On the other hand, if the claim reference is not found at block 444, then the exchange center system 100 recycles the record for a missing reference at block 452 and stores the record in the recycle review at block 454. It should be appreciated that recycle review at block 454 is similar to the recycle review at block 430 except that the recycle review block at 454 is when the system 100 is unable to successfully process the claim record due to a lack of a claim ID reference. Therefore, while recycling, the exchange center system 100 monitors for changes that could remedy or fix the error that caused the claim to be placed into the recycle review at block 454.

It should be appreciated that this process may be automatic (i.e. without human intervention) and may be accomplished using supervised or unsupervised machine learning. By way of an example and not limiting, a claim record that is in the recycle review at block 454 for failing the to identify a reference ID relating to the full reversal at block 442, the exchange center system 100 would monitor for any reference ID update and would automatically reprocess that claim from block 450 the next time the reference ID update is received. As such, if the update provides the reference ID, then the claim reference is added and the claim evaluated for meeting the plurality of rules of block 450, as discussed above.

It should be appreciated that the recycle review at block 454, as discussed above, continues to loop through a recycle period that can be adjustable. By way of an example and not limiting, the recycle period may be 30 days for one Vendor, 60 days for another vendor, and/or the like such that predetermined time periods for how long the claim may be recycled. Once the predetermined time period is exhausted without the claim record leaving the recycle review loop, the record is rejected at block 456 and a rejection response is provided back to the originating Claim Processing Vendor's at block 458. The response to the originating Claim Processing Vendor may include a reason for the rejection. By way of an example and not limiting, the response may include the reason of rejection being due to missing reference ID. As such, once the claim is rejected at block 458, the originating Claim Processing Vendor would again be responsible for the claim and for correcting the reasoning for why the claim failed.

If the claim fails the plurality of rules at block 450, the claims are recycled for failing the rules(s) at block 486 and are held in a recycle review 488. It should be appreciated that recycle review at block 488 is similar to the recycle review at blocks 430, 454 except that the recycle review block at 488 is when the system 100 is unable to successfully process the claim record due to the record failing at least one of a plurality of rules. Therefore, while recycling, the exchange center system 100 monitors for changes that could remedy or fix the error that caused the claim to be placed into the recycle review at block 488. If the rule is met or a change to the rule occurs, the exchange center system 100 would automatically add the claim reference and accept the claim at block 446. That is, if the update provides the deficient information or a change in the rule(s), then the claim reference is added and the claim is accepted at block 446, as discussed above.

Similar to the recycle review of blocks 430 and 454, once the predetermined time period is exhausted without the claim record leaving the recycle review loop, the record is rejected at block 490 and a rejection response is provided back to the originating Claim Processing Vendor's at block 492. The response to the originating Claim Processing Vendor may include a reason for the rejection. By way of an example and not limiting, the response may include the reason of rejection being due to the claim record or the reversal request not meeting the predetermined criterial or at least one of the plurality of rules. As such, once the claim is rejected at block 492, the originating Claim Processing Vendor would again be responsible for the claim and for correcting the reasoning for why the claim failed.

With reference back to FIG. 4, the partial adjustment model is when there is an adjustment at block 440 and the adjustment is a partial adjustment at block 460, the system 100 may then be utilized to adjust claims from vendors that can partially adjust original claims. To accomplish the partial adjustment of the original claims, a chain of adjustment claims that mirror the full reversal model are created. The manual adjustment model is based on making full reversals on logical claim chains without using reference information. On the Healthcare Risk Bearer's, (also known as plan sponsor's) side, the system 100 assists with benefit configuration. Healthcare Risk Bearers have the ability to carve out many aspects of their specific health plans to include more services like behavioral/mental health benefits, medical, pharmaceutical and durable medical equipment. The system 100 is able to integrate all of these different benefit configurations through the out of pocket integration system put in place.

Further details concerning the adjustment at block 440 will now be discussed with reference to illustrative method 600 in FIG. 6. When the claim record is the adjustment at block 440, the system 100 validates the partial adjustment at block 460. If validated, the claim is evaluated against a plurality of rules at block 450. The plurality of rules may include a cross check of the reference ID to the saved claim reference ID, the claim record or adjustment request may be verified against a set of rules established by Claim Processing Vendors or the Recipient Claim Processing Vendors so that the claim adjustment and/or full reversal is applied to the proper claim or is in the correct format, and/or the like. If the claim passes the plurality of rules at block 450, the system 100 generates a full reversal at block 462, the claim reference with the new paid claim is created with reference information and is accepted by the system 100 at block 464, a response is sent to the Recipient Claim Vendor in the form of a money reversal at block 466, the claims/member is staged for export at block 482 and the record is extracted at block 484.

It should be appreciated that the partial adjustment process mirrors the full reversal model by always generating a full reversal and providing a reference that the recipient vendor can handle. By way of example and not limiting, the original claim from the originating vendor is for $10.00, the partial adjustment from the originating vendor is −$4.00 and the claim is assigned a claim reference 12345. The system 100 sends this information to the recipient vendor while processing the processing the partial adjustment. The system 100 would create a full reversal for −$10.00 and for the previously generated claim reference number 12345. The system may then create a new paid claim of $6.00 and may assign the new claim a new claim reference number such as 67890. It should be appreciated that the system 100 delivers the full reversal with 12345 claim reference number so that the recipient knows to which claim the reversal applies along with the $6.00 new paid claim with the claim reference number 67890.

It should also be appreciated that that system 100 may be configured to handle multiple partial adjustments on either different claims or the same claim. By way of example and not limiting, if the originating vendor sends an additional partial adjustment for the same claim reference number 12345, such as −$3.00 this time, the system may generate a −$6.00 reversal referencing claim reference number 67890, create a new $3.00 paid claim for the difference and may assign this new a new claim reference number 98765. As such, the reversal including the claim with the claim reference number 67890 and the new claim with the claim reference number 98765 may be delivered to the recipient vender. It should be appreciate that the system 100 is configured to manage these adjustments as the adjustment is received by keeping track of the above described chain of claims as the claims are handled, treating each claim as a new full reversal and paid claim combination.

It should also be appreciated that under the partial adjustment model, the system 100 may be configured to bridge systems (i.e. originating Claim Vendors, Recipient Claim Vendors, and/or the like) who may be configured to perform partial adjustments with integrated systems (i.e. originating Claim Vendors, Recipient Claim Vendors, and/or the like) that cannot accept partial adjustments. That is, many vendors (i.e. originating Claim Vendors, Recipient Claim Vendors, and/or the like) systems require a full reversal out an original claim and do not accept dollar adjustments that are missing an appropriate reference to a previously serviced claim. As such, in some embodiments, the claims are received by the system 100 generally are tagged with an identifier by the originating Claim Vendor that is recognized at block 440 indicating that the incoming claim is an adjustment rather than a reversal.

It should further be appreciated that the system 100 may cross-reference claim IDs and reference claim numbers so that every time a vendor processes a claim, or when the system 100 generates a claim, that claim is given a unique claim reference number. As such, each vendor may track the unique claim reference number(s) in their system as a reference model to identify a particular claim and to be used as an identifier for reversals.

If the partial adjustment is not validated at block 460, then the exchange center system 100 recycles the record for the invalid adjustment at block 468 and stores the record in the recycle review at block 470. It should be appreciated that recycle review at block 470 is similar to the recycle review at blocks 430 and 454 except that the recycle review block at 470 is when the system 100 is unable to successfully process the claim record due to a lack of a partial adjustment validation. Therefore, while recycling, the exchange center system 100 monitors for changes that could remedy or fix the error that caused the claim to be placed into the recycle review at block 470.

It should be appreciated that this process may be automatic (i.e. without human intervention) and may be accomplished using supervised or unsupervised machine learning.

By way of an example and not limiting, a claim record that is in the recycle review at block 470 for failing the to validate the partial adjustment relating to the adjustment at block 440, the exchange center system 100 would monitor for adjustment update and would automatically reprocess that claim from block 450 the next time the adjustment update is received. As such, if the update provides the adjustment, then the system 100 would evaluate the claim against the plurality of rules as discussed above.

It should be appreciated that the recycle review at block 470, as discussed above, continues to loop through a recycle period that can be adjustable. By way of an example and not limiting, the recycle period may be 30 days for one Vendor, 60 days for another vendor, and/or the like such that predetermined time periods for how long the claim may be recycled. Once the predetermined time period is exhausted without the claim record leaving the recycle review loop, the record is rejected at block 472 and a rejection response is provided back to the originating Claim Processing Vendor's at block 474. The response to the originating Claim Processing Vendor may include a reason for the rejection. By way of an example and not limiting, the response may include the reason of rejection being due to missing adjustment information. As such, once the claim is rejected at block 474, the originating Claim Processing Vendor would again be responsible for the claim and for correcting the reasoning for why the claim failed.

If the partial adjustment claim fails the plurality of rules at block 450, the claims are recycled for failing the rules(s) at block 486 and are held in a recycle review 488. It should be appreciated that recycle review at block 488 is similar to the recycle review at block 470 except that the recycle review block at 488 is when the system 100 is unable to successfully process the claim record due to the record failing at least one of a plurality of rules. Therefore, while recycling, the exchange center system 100 monitors for changes that could remedy or fix the error that caused the claim to be placed into the recycle review at block 488. If the rule is met or a change to the rule occurs, the exchange center system 100 would automatically generate the full reversal at block 462, the claim reference with the new paid claim is created with reference information and is accepted by the system 100 at block 464, and a response is sent to the Recipient Claim Vendor in the form of a money reversal at block 466.

On the other hand, similar to the recycle review of block 470, if the claim adjustment is held in the recycle review at block 488 a predetermined time period without the claim record leaving the recycle review loop, the record is rejected at block 490 and a rejection response is provided back to the originating Claim Processing Vendor's at block 492. The response to the originating Claim Processing Vendor may include a reason for the rejection. By way of an example and not limiting, the response may include the reason of rejection being due to the claim record or the partial adjustment request not meeting the predetermined criterial or at least one of the plurality of rules. As such, once the claim is rejected at block 492, the originating Claim Processing Vendor would again be responsible for the claim and for correcting the reasoning for why the claim failed.

With reference back to FIG. 4, if the claim is determined to be a paid claim at block 438, then the claim is evaluated against a plurality of rules at block 450. Further details concerning the paid claim at block 438 and the plurality of rules at block 450 will now be discussed with reference to illustrative method 700 in FIG. 7. The plurality of rules may include a cross check of the reference ID to the saved claim reference ID, the claim record may be verified against a set of rules established by Claim Processing Vendors or the Recipient Claim Processing Vendors so that the paid claim is applied to the proper claim or is in the correct format, and/or the like. If the claim passes the plurality of rules at block 450, the claim record is accepted at block 476, a response is sent to the Recipient Claim Vendor at block 478, the claims/member is staged for export at block 482 and the record is extracted at block 484.

If the claim fails the plurality of rules at block 450, the claims are recycled for failing the rules(s) at block 486 and are held in a recycle review 488. It should be appreciated that recycle review at block 488 is similar to the recycle review at blocks 430, 454, and 477 except that the recycle review block at 488 is when the system 100 is unable to successfully process the claim record due to the record failing at least one of a plurality of rules. Therefore, while recycling, the exchange center system 100 monitors for changes that could remedy or fix the error that caused the claim to be placed into the recycle review at block 488. If the rule is met or a change to the rule occurs, the exchange center system 100 would automatically accept the claim record at block 476. That is, if the update provides the deficient information or a change in the rule(s), then the claim is accepted at block 446, as discussed above.

Similar to the recycle review of blocks 430, 454, and 477, once the predetermined time period is exhausted without the claim record leaving the recycle review loop, the record is rejected at block 490 and a rejection response is provided back to the originating Claim Processing Vendor's at block 492. The response to the originating Claim Processing Vendor may include a reason for the rejection. By way of an example and not limiting, the response may include the reason of rejection being due to the claim record or the reversal request not meeting the predetermined criterial or at least one of the plurality of rules. As such, once the claim is rejected at block 492, the originating Claim Processing Vendor would again be responsible for the claim and for correcting the reasoning for why the claim failed.

Figure 5:
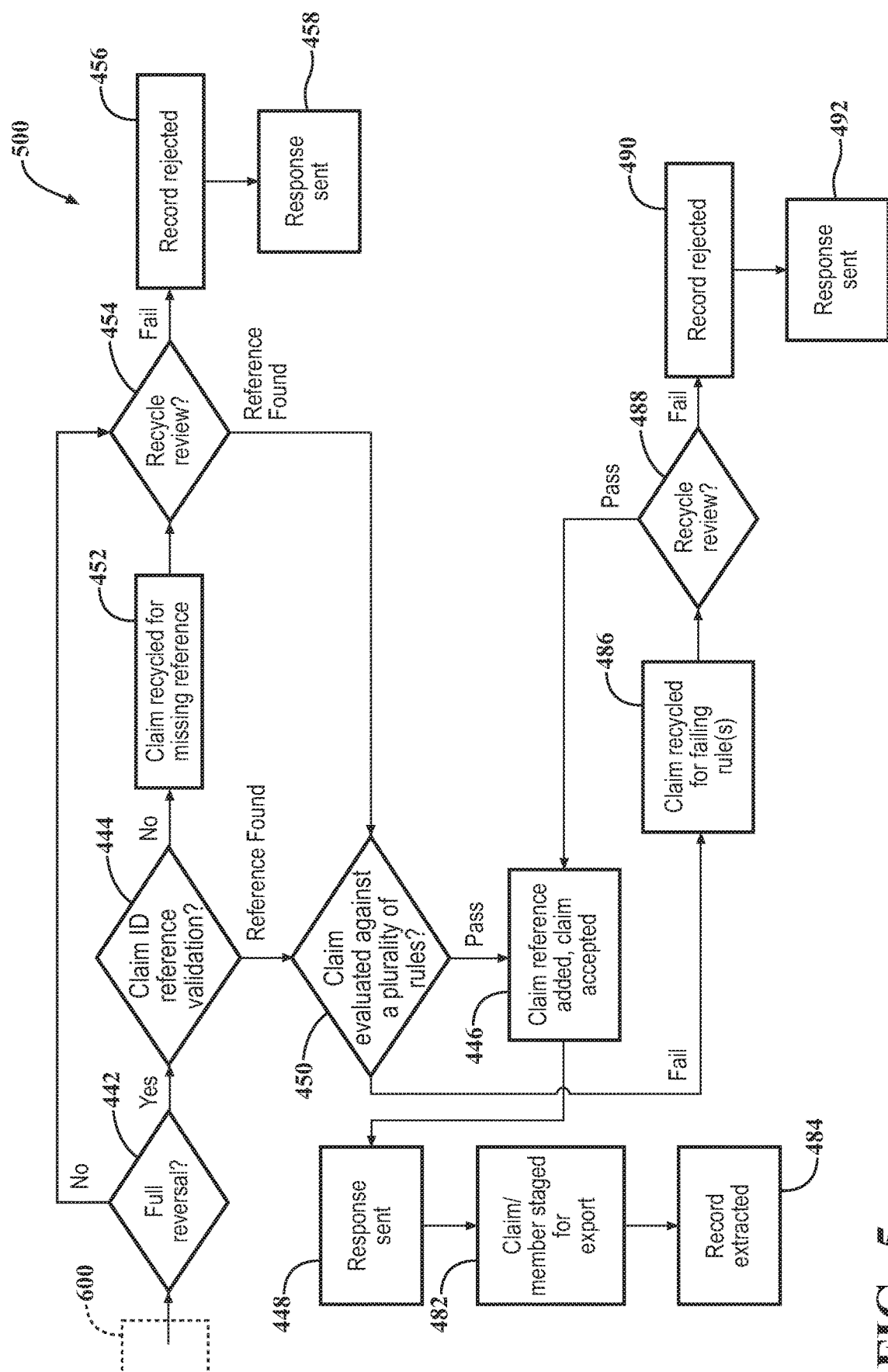
FIG. 5 depicts a flow diagram of an illustrative method of the full reversal of FIG. 4 according to one or more embodiments shown and described herein.
Figure 6:
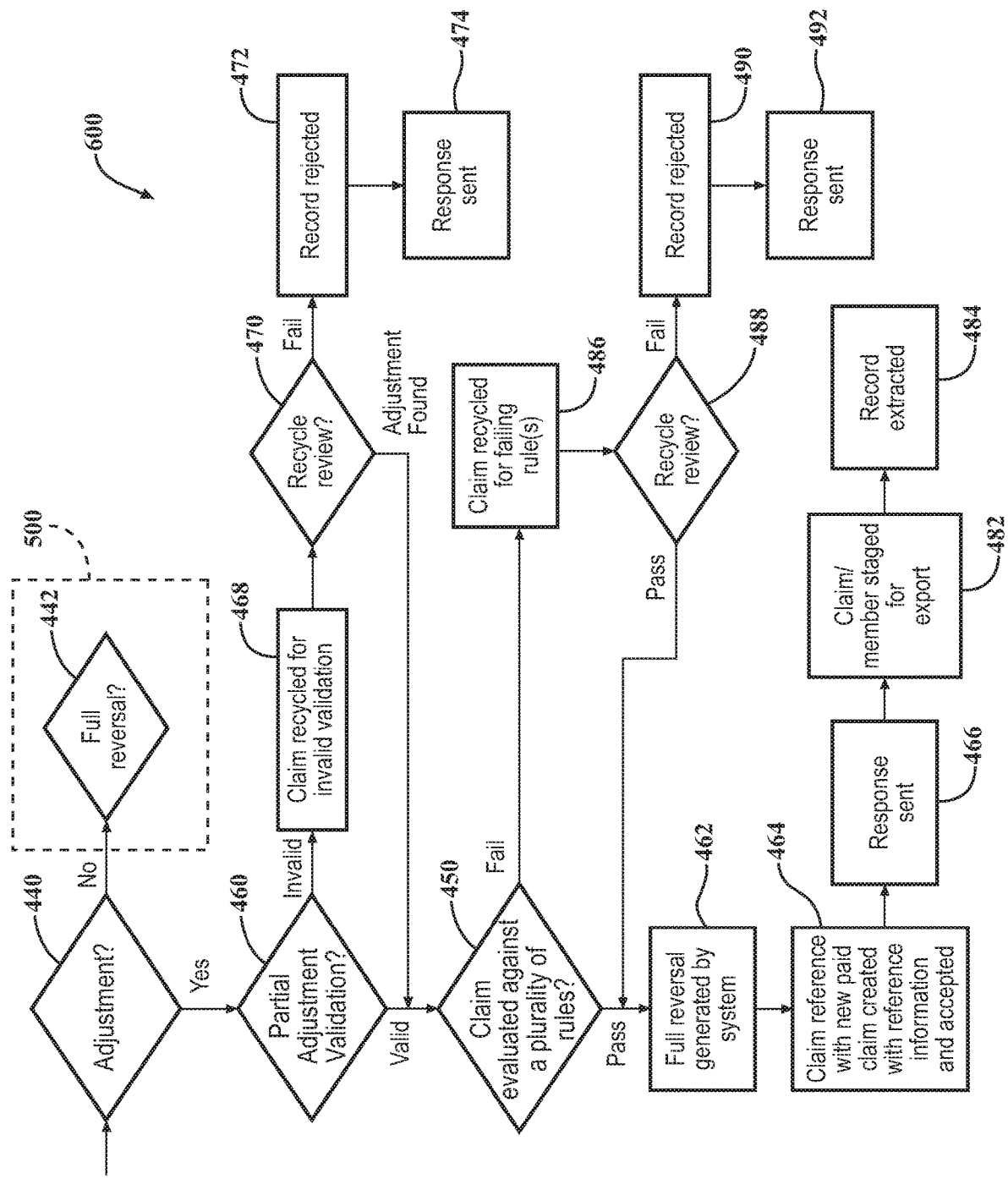
FIG. 6 depicts a flow diagram of an illustrative method of the adjustment of FIG. 4 according to one or more embodiments shown and described herein.
Figure 7:
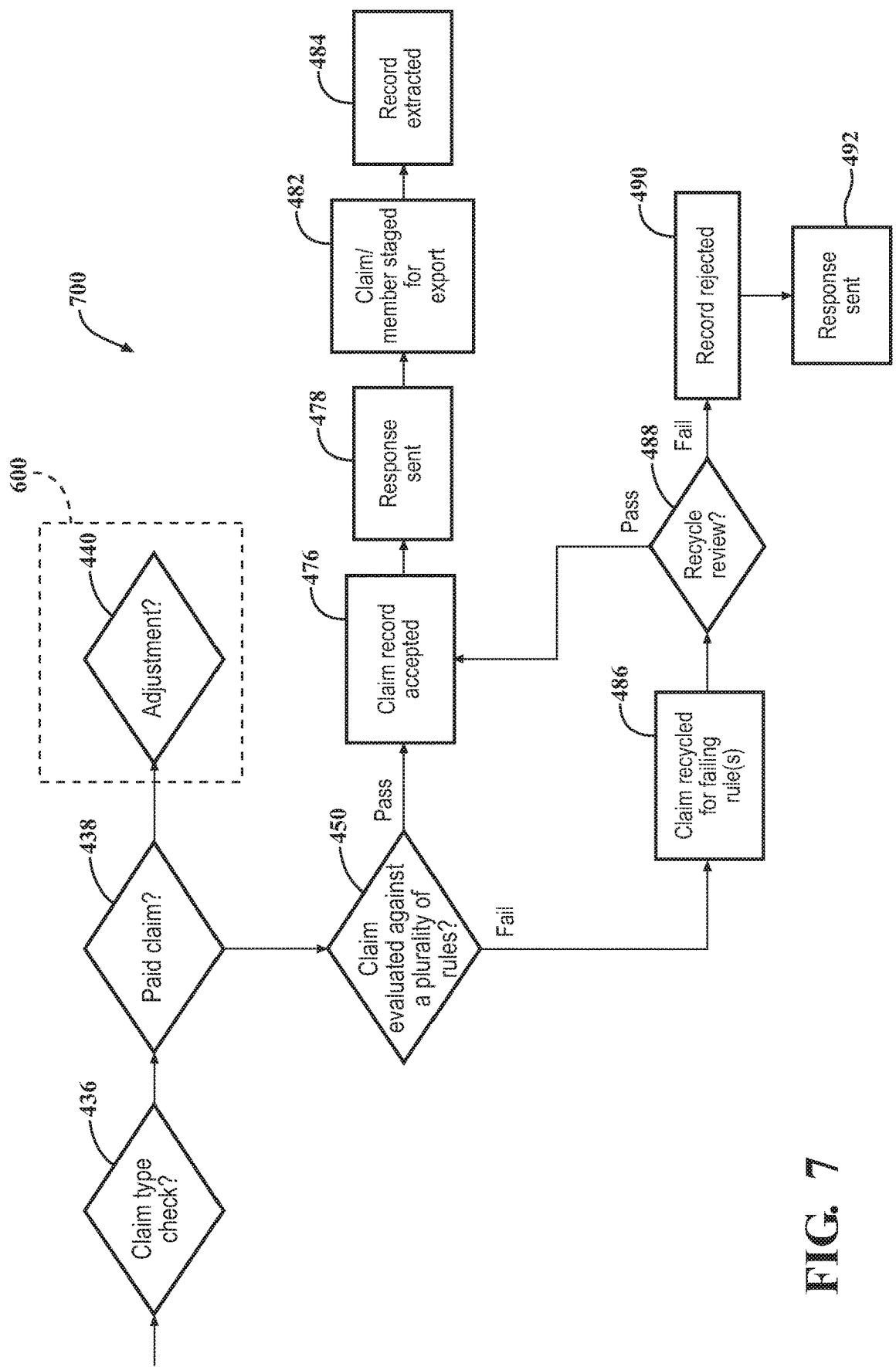
FIG. 7 depicts a flow diagram of an illustrative method of the paid claim of FIG. 4 according to one or more embodiments shown and described herein.

With reference to now FIGS. 5-7, it should be appreciated that the when the claim is evaluated against the plurality of rules at block 450, the data may be automatically analyzed by the system 100 to determine whether or not the claim will be accepted by the selected Recipient Claim Processing Vendor or whether or not the data meets certain predetermined criteria. That is, if all of the rules, criteria, and/or the like are met for submission to the Recipient Claim Processing Vendor, the claim may be accepted within each subroutine or process (i.e. 500, 600, and 700). The criteria may include a data format, a plurality of coding standards, a plurality of connectivity information, a manner in which the claim submission is forwarded to the plurality of Recipient Claim Processing Vendors, and/or the like. As such, when the claim is forwarded, the claim, the member, and/or the like is now staged for export to the appropriate Recipient Claim Processing Vendor at block 482 and the claim, the member, and/or the like is extracted having the system 100 information, data, and/or the like attached at block 484. The appropriate Recipient Claim Processing Vendor, if any, at block 482 may be determined based upon the eligibility data provided by each Claim Processing Vendor.

Further, in some embodiments, the system 100 at block 450 may either determine or translate the claim into the Claim Processing Vendor's preferred layout. The eligibility information of the originating Claim Processing Vendors claim may be translated to match the Recipient Claim Processing Vendor system and the appropriate eligibility information is inserted into the outgoing data claim using the crosswalk created by the system 100 between one Claim Processing Vendor's reference based eligibility model and a Recipient Claim Processing Vendor utilizing a coverage period based model.

The data transmission at block 484 may be accomplished by way of a secure connection with the originating Claim Processing Vendor using a variety of connectivity mechanisms. Claim Processing Vendors have a desired transport mechanism and frequency that cannot always be reconciled with other Claim Processing Vendors procedures. The system 100 will connect to the Claim Processing Vendors' systems using their preferred model and translate that to communicate data to Recipient Claim Processing Vendors. Data received by the system 100 may be immediately processed and an acknowledgement message is delivered to the originating Claim Processing Vendor to verify receipt of the data. Various Claim Processing Vendors have varying transmission systems with differing capabilities. Systems can range from real time data transmission to monthly batch file deliveries. Additional constraints may include file formats, allowable delivery windows, data transmission methods, security protocols, and/or the like. The system 100 enters each of the specifications into the database and manages all Claim Processing Vendor communications based upon the pre-established specifications. Once a claim is successfully processed, the system then checks the delivery specifications for each of the Recipient Claim Processing Vendors. The data is then transmitted in accordance with that configuration. Data for scheduled batch deliveries is staged and held until the next scheduled delivery at which time it is delivered. Data for real-time recipients may be immediately delivered over the appropriate channel.

It should be appreciated that while the system 100 has been depicted as processing claims for a single Claim Processing Vendors, this is non-limiting and the system 100 is configured to process the claim for multiple Claim Processing Vendors of coverages. As such, the eligibility validation at block 412 may include validating records from multiple vendors. Further, when processing the claim for multiple Claim Processing Vendors of coverages sponsored by the same Healthcare Risk Bearer, it may be necessary to ensure that there is integration of cost sharing so that cost limits such as out-of-pocket, deductible, coinsurance, etc. are not exceeded. Because each Claim Processing Vendor utilizes different methods of interpreting data and business processes, the system 100 provides a reconciliation process that ensures each Claim Processing Vendor's accumulated amount is synchronized. The reconciliation process compares momentary totals across all Claim Processing Vendors to ensure that the individual information is synchronized. This reconciliation process account for the timing of the claim files to reduce any discrepancies identified for errors of timeliness. By way of example and not limiting, one individual might appear out-of-sync between two of the Claim Processing Vendors because during the time the reconciliation files were prepared, a claim was in-transit from an originating Claim Processing Vendor to a Recipient Claim Processing Vendor, but not yet posted. In order to facilitate this reconciliation, the system 100 acts as a central hub importing the information from any originating Claim Processing Vendor and using each such Vendor's native layouts and processing goals. The system utilizes its alias matching at block 424 between each Claim Processing Vendor to ensure that records are being compared for the same individual in both systems to avoid unnecessary discrepancies caused by mismatched demographic information.

Further, when it is necessary to adjust or to reverse a claim, adjustments and reversals must be passed between each Claim Processing Vendor to ensure universal synchronization of data. Claim Processing Vendors have individual solutions for reversing and adjustment handling, so if one Claim Processing Vendor is unable to process adjustments and can only utilize reversals and another Claim Processing Vendor with which one Claim Processing Vendor coordinate uses adjustments, a translation from adjustments to reversals is required. The translation of an adjustment to a reversal generally includes a full reversal of the original claim followed by submission of a new claim with a new actual dollar amount. This may require multiple stages of submitting replacement claims to the original claim submittal. The system 100 automatically submits the replacement claims to the original claim submittal.

It should now be understood that when a Claim Processing Vendor adjudicates and delivers a claim, an assumption is made that the demographic information included in that claim is accurate and should be delivered to the recipient with the source vendor's data. The recipient Claim Processing Vendor will utilize its own interpretation of an individual's demographic data when validating an incoming record. This interpretation often differs from the source vendor due to different processing rules between the disparate systems. These different interpretations of an individual's demographic data can cause posting failures in the delivery of records. The chance of failure further increases with large membership populations. The system 100 remedies this issue through its use of vendor-specific aliases to effectively manage each Claim Processing Vendor's interpretation of member demographic data. When a claim can be successfully submitted to a Recipient Claim Processing Vendor, the claim is staged and released to each Recipient Claim Processing Vendor. When the claim data is released to a Recipient Claim Processing Vendor, the individual demographic information supplied is determined by pulling the most current alias for that individual as supplied by that Recipient Claim Processing Vendor. If no appropriate individual information exists to forward the claim, it will wait in a system holding area. A Recipient Claim Processing Vendor's individual information is automatically monitored for any changes. When the Recipient Claim Processing Vendor provides an update to individual information that allows an alias to be placed on the claim, then the claim will be automatically released and included in the next transmission.

It should now be understood that that disclosed is methods and systems automated handling of claims between multiple Claim Processing and Recipient Vendors. The system permits proper and accurate delivery of claims in accordance with the requirements of each of the Claim Processing Vendors. The claims are checked for accuracy and forwarded in accordance with the Claim Processing Vendors' rules. The system also allows the sharing of cost values and any necessary adjustments. To monitor the overall accuracy of the data feeds, the system provides inventory management and reporting services to maintain synchronization amongst all Claim Processing Vendors servicing a Health Risk Bearer.

We claim:

1. A computer machine system having one or more computer machines wherein said computer machine system comprises:

one or more processors;

at least one first computer non-transitory, processor-readable storage medium having one or more programming instructions thereon, the at least one first computer storage medium configured to store:
- a plurality of eligibility data for a plurality of individuals associated with a group healthcare plan in a first data format;
- a set of user identifiers, wherein each user identifier is associated with:
  - a specific user;
  - one or more demographic information from the specific user; and
  - one or more individual eligibility data from said plurality of eligibility data; and at least one second computer non-transitory, processor-readable storage medium having one or more programming instructions thereon, the at least one second computer storage medium configured to store:
- a first plurality of rules for a claim submission associated with each group healthcare plan, the first plurality of rules include instructions for translating the first data format to the claim submission for at least one of a plurality of originating payors associated with the claim submission and into a second data format and for translating in reverse into an original data format;
- a second plurality of rules for a processed claim submission associated with each of the plurality of originating payors, the second plurality of rules includes instructions for translating the second data format into a third data format for the processed claim submission for a plurality of recipient payors associated with the processed claim submission and for translating in reverse from the third data format into the second data format, wherein each of the plurality of recipient payors having at least one second data submission requirement associated with the processed claim submission for the plurality of recipient payors such that the third data format conforms to the at least one second data submission requirement, the third data format being different from the second data format, wherein the one or more programming instructions of the at least one first computer storage medium or the at least one second computer storage medium, when executed, cause the one or more processors to:
- translate automatically the first data format using the first plurality of rules,
- translate automatically the first data format into the second data format using the first plurality of rules for the processed claim submission associated with each one of the plurality of recipient payors, and
- translate automatically the second data format and the third data format using the second plurality of rules and the first plurality of rules in reverse into the original data format such that the original data format is mapped to the at least one first computer storage medium to notify the group healthcare plan of an outcome of the claim submission.

2. The computer machine system of claim 1, wherein the first plurality of rules associated with the claim submission include a data format, a plurality of coding standards, a plurality of connectivity information, and a manner in which the claim submission is forwarded to the plurality of recipient payors.

3. The computer machine system of claim 1, wherein each one of the claim submissions is forwarded to the plurality of recipient payors based on the first plurality of rules for each one of the claim submissions associated with each group healthcare plan.

4. The computer machine system of claim 3, wherein each one of the claim submissions by the plurality of originating payors is posted in the second computer storage medium.

5. The computer machine system of claim 4, wherein each one of the processed claim submissions that meets the at least one second data submission requirement associated with the processed claim submission for the plurality of recipient payors are released for transmission to the plurality of recipient payors.

6. The computer machine system of claim 4, wherein each one of the processed claim submissions that fails to meet the at least one second data submission requirement associated with the processed claim submission for the plurality of recipient payors are held from transmission to the plurality of recipient payors until sufficient data is received such that the processed claim submissions meet the at least one second data submission requirement for the plurality of recipient payors.

7. The computer machine system of claim 6, wherein the system continuously searches for missing data for each one of the processed claim submissions that are held from transmission to the plurality of recipient payors until sufficient data is received such that the processed claim submissions meets the at least one second data submission requirement for the plurality of recipient payors.

8. The computer machine system of claim 1, further comprising:
    the at least one second computer storage medium configured to store:
        a third plurality of rules, the third plurality of rules associated with the processed claim submission for each one of the plurality of recipient payors, the third plurality of rules includes a plurality of full claim reversal rules and a plurality of partial adjustment rules specific to each one of the plurality of recipient payors.

9. The computer machine system of claim 8, wherein the system generates a reference number specific to at least one of the plurality of recipient payors upon a full claim reversal of the processed claim submission that meets the plurality of full claim reversal rules.

10. The computer machine system of claim 9, wherein a partial adjustment to the processed claim submission utilizes a chain of adjustment claims such that the partial adjustment is made when the partial adjustment with the chain of adjustment claims meets a plurality of partial adjustment rules.

11. The computer machine system of claim 1, wherein the one or more computer machines is configured to integrate a plurality of co-pays and a plurality of deductibles based on the plurality of eligibility data for the plurality of individuals associated with the group healthcare plan and the set of user identifiers.

12. A computer machine implemented automated claim processing comprising the steps of:
    receiving a plurality of eligibility data for a plurality of individuals associated with a group healthcare plan;
    storing, by one or more processors, the plurality of eligibility data onto at least one first computer non-transitory, processor-readable storage medium having one or more programming instructions thereon, as a first data format;
    receiving and storing, by the one or more processors, onto at least one second computer non-transitory, processor-readable storage medium having one or more programming instructions thereon, a first plurality of rules for a claim submission associated with each group healthcare plan, the first plurality of rules include instructions for translating the first data format to the claim submission for at least one of a plurality of originating payors associated with the claim submission and into a second data format and for translating in reverse into an original data format;

receiving and storing, by the one or more processors, onto the at least one second computer storage medium, a second plurality of rules for a processed claim submission associated with each of the plurality of originating payors, the second plurality of rules includes instructions for translating the second data format into a third data format for the processed claim submission for a plurality of recipient payors associated with the processed claim submission and for translating in reverse from the third data format into the second data format, wherein each of the plurality of recipient payors having at least one second data submission requirement associated with the processed claim submission for the plurality of recipient payors such that the third data format conforms to the at least one second data submission requirement, the third data format being different from the second data format, receiving a healthcare related claim for at least one of the plurality of individuals associated the group healthcare plan from the at least one of an originating claim Processing Vendor, the healthcare related claim includes a healthcare claim data;

determining whether the healthcare related claim is matched to a known individual based on comparing the healthcare claim data to the first data format;

extracting, by the one or more processors, a plurality of required information for a claim submission from the first data format stored on the at least one first computer storage medium to translate into the second data format that conforms to the first plurality of rules associated with the claim submission for each of the plurality of recipient payors;

determining, based on the first data format or the second data format, which of the plurality of recipient payors the healthcare claim is forwarded, translating automatically, by the one or more processors, the received healthcare related claim in the at least one first computer storage medium using required information for the claim submission for each one of the plurality of recipient payors;

translating automatically, by the one or more processors, the second data format to conform with the first plurality of rules for the processed claim submission associated for the plurality of recipient payors and for each subsequent recipient payor of the plurality of recipient payors;

translating automatically, by the one or more processors, the second data format and the third data format using the second plurality of rules and the first plurality of rules in reverse into the original data format; and communicating to each one of the plurality of recipient payors the second data and the third data format that independently meets the each one of requirements for the plurality of recipient payors and communicating, in the original data format, an outcome of the claim submission to the originating claim Processing Vendor.

13. The computer machine implemented automated claim processing process of claim 12, further comprising the step of:

analyzing the healthcare claim data to determine whether or not the healthcare claim will be accepted by the plurality of recipient payors, wherein the healthcare claim is accepted based on a predetermined criteria.

14. The computer machine implemented automated claim processing process of claim 13, wherein when the healthcare claim data is accepted based on the predetermined criteria, the healthcare claim is permitted to be transmitted to the at least one of the plurality of recipient payors.

15. The computer machine implemented automated claim processing process of claim 13, wherein when the healthcare claim data is rejected based on the predetermined criteria, the healthcare claim is staged in the at least one first computer storage medium.

16. The computer machine implemented automated claim processing process of claim 13, wherein the predetermined criteria includes a data format, a plurality of coding standards, a plurality of connectivity information, and a manner in which the claim submission is forwarded to the plurality of recipient payors.

17. The computer machine implemented automated claim processing process of claim 12, further comprising the steps of:

establishing a list of aliases associated with the plurality of individuals; and developing an enrollment roster for the at least one of the plurality of originating payors, wherein the list of aliases is used to determine a plurality of variants by comparing the individuals demographics to the enrollment roster.

* * * * *